United States Patent [19]

Boyars

[11] 4,359,399

[45] Nov. 16, 1982

[54] TAGGANTS WITH EXPLOSIVE INDUCED MAGNETIC SUSCEPTIBILITY

[75] Inventor: Carl Boyars, Silver Spring, Md.

[73] Assignee: The United States of America as represented by the Secretary of the Air Force, Washington, D.C.

[21] Appl. No.: 181,924

[22] Filed: Aug. 27, 1980

[51] Int. Cl.³ .................... G01N 33/22; C09K 3/00
[52] U.S. Cl. ................................. 252/408; 149/2
[58] Field of Search ................. 149/2, 2 T; 252/408

[56] References Cited

U.S. PATENT DOCUMENTS

| | | | |
|---|---|---|---|
| 3,772,200 | 11/1973 | Livesay | 252/301.1 R |
| 3,837,942 | 9/1974 | Catanzarite | 149/83 |
| 4,027,052 | 5/1977 | Thompson | 427/43 |
| 4,053,433 | 10/1977 | Lee | 252/408 |
| 4,131,064 | 12/1978 | Ryan et al. | 149/2 |
| 4,197,104 | 4/1980 | Krystyniak et al. | 149/2 |
| 4,198,307 | 4/1980 | Berkowitz et al. | 149/2 |
| 4,222,330 | 9/1980 | Krystyniak | 149/2 |

FOREIGN PATENT DOCUMENTS 2651528  5/1977  Fed. Rep. of Germany ...... 252/408

OTHER PUBLICATIONS

Achter et al., "Explosives Tagging and Control", (Second Annual Report, F.Y., 1978), 55 pp. Aerospace Report No. ATR-78 (3860-01)-IND. (1978).

*Primary Examiner*—Edward A. Miller
*Attorney, Agent, or Firm*—Donald J. Singer; William J. O'Brien

[57] ABSTRACT

A color-coded taggant for the post-detonation identification of explosive material. Retrieval of the taggnt after detonation of an explosive is facilitated by the addition of nickel formate to the taggant. The additive renders the taggant magnetically susceptible only after detonation. This eliminates the possiblity of the unauthorized removal of the taggant by a magnet before detonation but retains the advantages of facile retrieval by means of a magnet subsequent to detonation.

3 Claims, No Drawings

4,359,399

TAGGANTS WITH EXPLOSIVE INDUCED MAGNETIC SUSCEPTIBILITY

STATEMENT OF GOVERNMENT INTEREST

The invention described herein may be manufactured and used by or for the Government for governmental purposes without the payment of any royalty thereon.

BACKGROUND OF THE INVENTION

This invention relates to a method for labeling an explosive medium with a readily identifiable, coded indicator which can be utilized to identify the explosive after its detonation. In a more particular aspect this invention concerns itself with the coded tagging of explosives for post-detonation identification and the ready identification and retrieval of a color-coded taggant from a detonated explosive medium.

Preventing and controlling the illegal use of explosives has become a problem of paramount importance for law enforcement, regulatory and other government agencies. As a consequence, a considerable research effort has been under taken in an attempt to provide means and methods for detecting and identifying explosives both before and after their detonation. Considerable success has been achieved and a number of labeling and tracing methods have evolved for identifying many explosives. For example, the use of microparticles having a combination of coded tagging elements incorporated within the body of the microparticle is shown in U.S. Pat. No. 3,772,200. Tagging explosives with organic particles is shown in U.S. Pat. No. 3,897,284 while U.S. Pat. No. Re. 29,334 illustrates the use of phosphors for providing explosives with a distinctive information level. These methods, however, suffer certain disadvantages because of difficulty in retrieving and identifying the coded materials. Oftentimes they require expensive and complicated analytical equipment in order to "read" the code.

Another method for identifying explosives, however, has been demonstrated by the 3M Company and includes the use of a multilayered color-coded microparticle. U.S. Pat. No. 4,053,433 illustrates this concept. This patent also suggests the use of a fluorescent color in the color code and the incorporation of magnetic oxide or iron particles in the taggant to facilitate retrieval of the color-coded microparticle for identification through the use of a microscope or magnifying glass. Unfortunately, the utilization of a magnetic substance permits the removal of the taggant prior to detonation thereby subverting the original purpose of using the taggant as an identification aid. Unscrupulous individuals, with the aid of a strong magnet, could easily remove the color-coded taggants from a granular explosive, e.g. smokeless or black powder.

In accordance with the present invention, however, the early or pre-detonation removal of magnetic susceptible taggants has been solved by replacing the magnetic material with a compound that is rendered magnetic only after detonation of the explosive. Before detonation this material is non-magnetic and only develops its magnetic properties under the effects of shock and fireball heating that occur during detonation of the explosive.

SUMMARY OF THE INVENTION

The present invention provides for the post-detonation identification of explosive materials by means of a readily identifiable color-coded microparticle which can be decoded by visual inspection using a microscope or magnifying glass. Retrieval of the microparticles from an explosive medium are facilitated by incorporating nickel formate into the microparticle. This provides it with a magnetic susceptibility only after the explosive medium has been detonated. The magnetic characteristics of the microparticle or taggant makes it relatively easy for law enforcement personnel to recover it. On the other hand, since it does not possess any magnetic susceptibility until after detonation, the problem of the unauthorized removal of the taggant, by means of a magnet before detonation, is overcome. In accordance with the invention, it has been found that the incorporation of nickel formate, preferably in the outer layer of a multilayer color-coded taggant, provides the means for imparting an explosive-induced magnetic susceptibility to the taggant only after detonation.

Accordingly, the primary object of this invention is to provide a means for the identification of explosive materials subsequent to their detonation.

Another object of this invention is to provide a means for facilitating the post-detonation retrieval of color-coded taggants from an explosive medium.

Still another object of this invention is to provide a color-coded, magnet sensitive taggant for use in the post-detonation identification of explosive materials.

A further object of this invention is to provide a color-coded taggant characterized by having an explosive-induced magnetic susceptibility only after detonation of an explosive medium.

The above and still further objects and advantages of the present invention will become more readily apparent upon consideration of the following detailed disclosure when viewed in conjunction with the accompanying drawings.

DESCRIPTION OF THE DRAWING

In the Drawings:

FIG. 1 is a schematic illustration of the type of color-coded explosives taggant contemplated by this invention; and FIG. 2 is a schematic color illustration of a suggested color coding sequence suitable for use in identifying the coded taggant of FIG. 1.

DETAILED DESCRIPTION OF THE PREFERRED EMBODIMENT

The basis for the present invention revolves around the fact that the tagging of explosives for post detonation identification has become an important tool for law enforcement officers and the various governmental agencies concerned with the emergence of the bomb as a terrorist weapon.

Prior research has indicated that there are fundamental limitations in our ability to detect explosives before detonation or to identify them after detonation. The problem with post-detonation identification of explosives is that detonation often leaves no chemical residue at all, much less any residue specific to a given production lot.

Research on post-detonation identification of residue has been a continuing task of forensic laboratories. Today, highly sophisticated methods such as high-performance liquid chromatography and mass spectrometry are used. But they are limited to a determination of the generic explosive type, and in a very rare case, the name of the manufacturing plant. This limitation, as in the case of detection, is inherent in the nature of the material from which explosives are made.

Concurrent with the efforts described above, researchers began to look for an adulterant which could be used to seed or tag explosives to make them more easily detectable and identifiable. The first studies involved radioactive sources such as $^{60}$Co. Later suggestions included readily activated materials (such as gadolinium), electromagnetic resonators, and remote deactivation techniques. In recent years, the applicability of x-ray fluorescing taggants have been explored. In general, explosives identification tagging refers to the addition of tiny coded particles to explosives during their manufacture. These particles or taggants can survive detonation and be recovered and decoded. Through distribution records, they allow the explosives to be traced back to the last legal possessor. This information can provide critical evidence to investigators of criminal bombings. Even where distribution of a lot of explosive is so widespread that there are many final legal possessors, as is the case with sporting grades of black powder and with smokeless powder for handloaders, identification taggants would provide useful clues for tracing.

One type of taggant for post-detonation which is now being evaluated on a fairly large scale was developed by 3M Company. The taggant is a multilayered particle in which the layers differ in color as shown in FIG. 1 to coincide with a color code as indicated in FIG. 2. When viewed through a microscope, the code can be identified by the colors that are selected from a library of 10 colors and assigned numbers corresponding to the electrical resistor color code. For a nine-layer taggant, the number of possible colored-layer permutations and combinations is 100 million in the absence of any restrictions. When suitable limitations are imposed, relating to adjacent colors and the requirements for a dark magnet-sensitive layer, a total of 2,008,519 combinations remain. This final number is available with each of three fluorescent layers (discussed below); hence, the total taggant library is 6,025,557.

The basic 3M taggant consists of a laminated melamine alkyd core. The core is color-coded by the inclusion of various pigments. One of the layers normally includes iron particles to make the taggant magnet-sensitive, and one or both exterior layers may include one of three fluorescers which respond to UV irradiation.

In order to reduce the possibility of interaction between taggant and explosive and also to increase the survival rate of taggants by attenuating the shock wave of a detonation, the taggant can be encapsulated with polyethylene wax. The polyethylene wax is normally absent from taggants recovered after detonation. However, it has been found that the unencapsulated 3M Type taggant does not sensitize explosives or make them unstable and that the polyethylene wax encapsulant taggant dissolves after fairly short storage periods in dynamite without affecting taggant survivability on detonation. Therefore, the unencapsulated type taggant can be used in scenarios where it is more advantageous than the encapsulated taggant.

Another variant of the color-coded taggant is a form which includes a magnetic sensitive (ferromagnetic) component. For explosive powders (i.e., block powder, smokeless powder, and the oxidizer portion of two-component explosives), use of a magnet to remove the ferromagnetic taggant prior to detonation by unauthorized personnel is a possibility. In these cases, a magnetic-insensitive taggant may be required despite the much greater difficulty for an investigator or law enforcement officer to recover such a taggant.

In order to realize the advantage of easy taggant recovery provided by a magnet-sensitive layer while eliminating the possibility of a magnet being used to separate the taggant from explosive powders prior to detonation, it was found that the incorporation of a compound which will become ferromagnetic upon being subjected to the shock and fireball heating of an explosive would be successful. The particular compounds found to produce the desired explosive induced magnetic susceptibility are Ferrocene (dicyclopentadienyl iron) and nickel formate. These components become magnetic susceptible under shock and fireball heating. The nickel formate is particularly desirable since it becomes magnetic susceptible at temperatures low enough such that the melamine alkyl laminate of the 3M taggant is not charred and its color coding thereby destroyed. The nickel formite is converted to a magnetic susceptible species by heating at 246° C. and the color code of the 3M taggant is not affected. The nickel formate is preferably incorporated in the outer fluorescent containing layer of the taggant as shown in FIG. 1 and can be added in amounts of up to about 30 weight percent of the taggant microparticle.

The taggant can be added to the explosive medium in amounts of about 0.05 to 0.1 weight percent during manufacture with a suitable color code, as shown in FIG. 2, such that the proportion batch and manufacturing location of the batch can be determined at a later date by law enforcement personnel. For example, pipe bombs filled with black or smokeless powder are often used by criminal bombers presumably because of the ready availability of these explosives which have a wide retail distribution. The most readily available and convenient form for such illicit use is in the powders supplied for handloaders: smokeless powder for modern firearms and black powder for antique and replica muzzle-loading weapons.

Because black and smokeless powders are used as propellants, not only must the criteria for the identification tagging of other explosives be met, but also other criteria related to performance in firearms. Thus, it must be established not only that the taggants can be added in the powder manufacturing processes safely, uniformly, and with minimal cross-contamination, but also that the effects of taggants on ballistic variations, on the fouling of guns, and on the wear of guns are negligible. In addition, because these powders are granular, the possibility exists that taggants might become segregated during normal storage and handling or other illicit users might seek to remove the taggants.

To determine whether taggants distributed in double-base smokeless powder and in analogous black powder could be recovered and identified after explosion, tests were conducted using capped pipes and various modes of initiation. Identification of the recovered 3M taggants was made for each test condition. In carrying out the tests, 3-lb charges of powder were mixed with 0.05 percent taggant, which were then placed in Schedule 40, 3-in-diameter, capped pipes of lengths suitable to just contain the charges (19 in. for the smokeless and 11 in. for the black powder). GOEX, FFFg Supertine Black Rifle Powder were used because that granulation is the major product used by muzzle loaders. Hercules "Bullseye" smokeless powder was used because it is the fastest burning and the most energetic (nominal 40-percent nitroglycerin content) and therefore provided the most severe test of taggant suvivability. The capped pipes were exploded on a large sand pile in a semicylindrical tank facility. After each shot, a team recovered the taggants that had survived the explosion, using ultraviolet fluorescence, a magnetic broom, and purely mechanical methods. The recovered taggants were separated from the debris and the codes read by referring to a color code such as that illustrated in FIG. 2.

The sequence of pipe explosion tests is shown in Table I.

TABLE I

SEQUENCE OF PIPE EXPLOSION TESTS

| Test Number | Powder Type (all 3 lb) | Pipe Length (in.) | Initiation |
|---|---|---|---|
| 1 | Smokeless | 19 | Squib |
| 2 | Black | 11 | Squib |
| 3 | Smokeless | 19 | Hobby Fuse-19 in. in pipe; 24-in. lead |
| 4 | Black | 11 | Hobby Fuse-11 in. in pipe; 24-in. lead |
| 5 | Smokeless | 19 | Safety Fuse-19 in. in pipe; 24-in. lead |
| 6 | Black | 11 | Safety Fuse-19 in. in pipe; 24-in. lead |
| 7 | Smokeless | 19 | Blasting Cap |
| 8 | Black | 11 | Blasting Cap |
| 9 | Smokeless | 19 | Blasting Cap |
| 10 | Smokeless | 19 | Blasting Cap |

The tagging of explosives for post-detonation identification is an important aid to investigators of criminal bombings. One requirement for such taggants is that they are magnetic in order to facilitate their recovery from the explosion debris. Identification tagging of smokeless and black powders, however, presents a dilemma since, if the taggant is magnet sensitive, it can readily be removed before filling pipe bombs. On the other hand, if the taggant is not magnet sensitive, post-detonation recovery by law enforcement personnel becomes much more difficult.

With the novel feature of this invention, however, the prevention of the removal of the taggant from powder and granular explosives by use of a magnet, coupled with the retention of a capability of recovering the taggant from explosive debris by its magnetic response is accomplished. This accomplishment is due to the use of materials which are not magnetic but which become magnetic in the course of the explosion; and it is this feature that constitutes the novelty of the invention.

In general, the amount of additive necessary to render the color-coded taggants magnetically susceptible after detonation of a taggant containing explosive is relatively small and the specific amounts required can be determined easily for each type of explosive material to be tagged.

While the invention has been described by reference to a particular embodiment, it should be understood by those skilled in the art that various modifications and alterations can be resorted to and that all such modifications as are encompassed within the scope of the appended claims are intended to be included herein.

What is claimed is:

1. In a color-coded explosive taggant consisting essentially of a plurality of laminated layers of a resinous material in which each layer differs in color according to a sequence corresponding to a preconceived color code thereby enabling visual identification of said color-coded taggant, the improvement which comprises the addition of a minor amount of an explosion induced, magnetically susceptible, nickel formate to at least one of said laminated layers.

2. A color-coded explosive taggant in accordance with claim 1 wherein said laminated layers are composed of a melamine alkyl resin.

3. A color-coded explosive taggant in accordance with claim 1 wherein said nickel formate is added in amounts up to about 30 weight percent of said explosives taggant.

* * * * *